(12) United States Patent
Broome et al.

(10) Patent No.: US 7,632,305 B2
(45) Date of Patent: Dec. 15, 2009

(54) BIODEGRADABLE CONNECTORS

(75) Inventors: Thomas E. Broome, Prior Lake, MN (US); Daniel Gregorich, St. Louis Park, MN (US); Adam Jennings, Buffalo, MN (US); Michael P. Meyer, Richfield, MN (US); John Blix, Maple Grove, MN (US); Gordon J. Kocur, Lino Lakes, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 164 days.

(21) Appl. No.: 11/773,991

(22) Filed: Jul. 6, 2007

(65) Prior Publication Data

US 2009/0012599 A1 Jan. 8, 2009

(51) Int. Cl.
*A61F 2/06* (2006.01)
(52) U.S. Cl. .................... 623/1.35; 623/1.38
(58) Field of Classification Search ........ 623/1.35–1.54
See application file for complete search history.

(56) References Cited

U.S. PATENT DOCUMENTS

| | | | |
|---|---|---|---|
| 5,358,475 A | 10/1994 | Mares et al. | |
| 6,258,117 B1 | 7/2001 | Camrud et al. | |
| 6,331,189 B1 * | 12/2001 | Wolinsky et al. | 623/1.15 |
| 6,409,750 B1 * | 6/2002 | Hyodoh et al. | 623/1.1 |
| 6,409,754 B1 | 6/2002 | Smith et al. | |
| 7,022,132 B2 | 4/2006 | Kocur | |
| 7,452,372 B2 * | 11/2008 | Miller | 623/1.35 |
| 2002/0107560 A1 | 8/2002 | Richter | |
| 2004/0059406 A1 | 3/2004 | Cully | |
| 2004/0138737 A1 | 7/2004 | Davidson et al. | |
| 2005/0043816 A1 | 2/2005 | Datta et al. | |
| 2005/0102023 A1 | 5/2005 | Yadin et al. | |
| 2007/0055362 A1 | 3/2007 | Brown | |
| 2007/0067019 A1 * | 3/2007 | Miller et al. | 623/1.16 |
| 2007/0067023 A1 * | 3/2007 | Kveen et al. | 623/1.35 |
| 2008/0281395 A1 * | 11/2008 | Eidenschink et al. | 623/1.11 |
| 2009/0036820 A1 * | 2/2009 | Dakin et al. | 604/9 |

FOREIGN PATENT DOCUMENTS

| | | |
|---|---|---|
| EP | 1 563 806 A1 | 8/2005 |
| WO | 2005/032424 A1 | 4/2005 |
| WO | 2005/102220 A1 | 11/2005 |
| WO | 2005/118971 A2 | 12/2005 |
| WO | 2006/087621 A1 | 8/2006 |

* cited by examiner

*Primary Examiner*—Suzette J Gherbi
(74) *Attorney, Agent, or Firm*—Vidas, Arrett & Steinkraus P.A.

(57) ABSTRACT

An expandable bifurcated stent is formed of a main body and a first branch. The body wall is made up of interconnected stent members that define a plurality of cells, at least one of which is a side opening. The first branch body extends from the body wall from at least two regions adjacent the side opening. At least one stent member adjacent the perimeter is bioabsorbable.

15 Claims, 17 Drawing Sheets

BIODEGRADABLE CONNECTORS

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Stents and similar devices such as stent, stent-grafts, expandable frameworks, and similar implantable medical devices, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. § 1.56(a) exists.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY

Embodiments of the invention are directed to a bifurcated stent having an unexpanded state and an expanded state. The stent comprises a main body with a body wall. The body wall extends along a main longitudinal axis from a proximal end to a distal end and defines a lumen between the two ends. The body wall is comprised of interconnected stent members, a plurality of which defines a plurality of cells. At least one of the cells is a side opening having a perimeter. The side opening is shaped differently then the other cells of the stent.

The stent also comprises a first branch having a first branch body. The first branch body is positioned between the distal end and the proximal end of the main body and extends along a first branch longitudinal axis when the stent is in the expanded state. Furthermore, the first branch body extends from the body wall from at least a first region adjacent the side opening and a second region adjacent the side opening. At least one of the stent members adjacent the perimeter is bioabsorbable.

In some embodiments, the stent includes deflectable members which extend from the main body at positions about the perimeter of the side opening.

In at least one embodiment, the side opening perimeter includes a bioabsorbable expansion joint.

In at least one embodiment, the body wall comprises a plurality of circumferential rings, longitudinally offset from one another about the main longitudinal axis. The first branch body also comprises at least one branch ring being arranged about the first branch axis and extending from the perimeter of the side opening by at least one bioabsorbable stent member.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

FIG. 1b is a cross-sectional view of the embodiment depicted in FIG. 1a.

DETAILED DESCRIPTION OF THE INVENTION

Figure 1A:
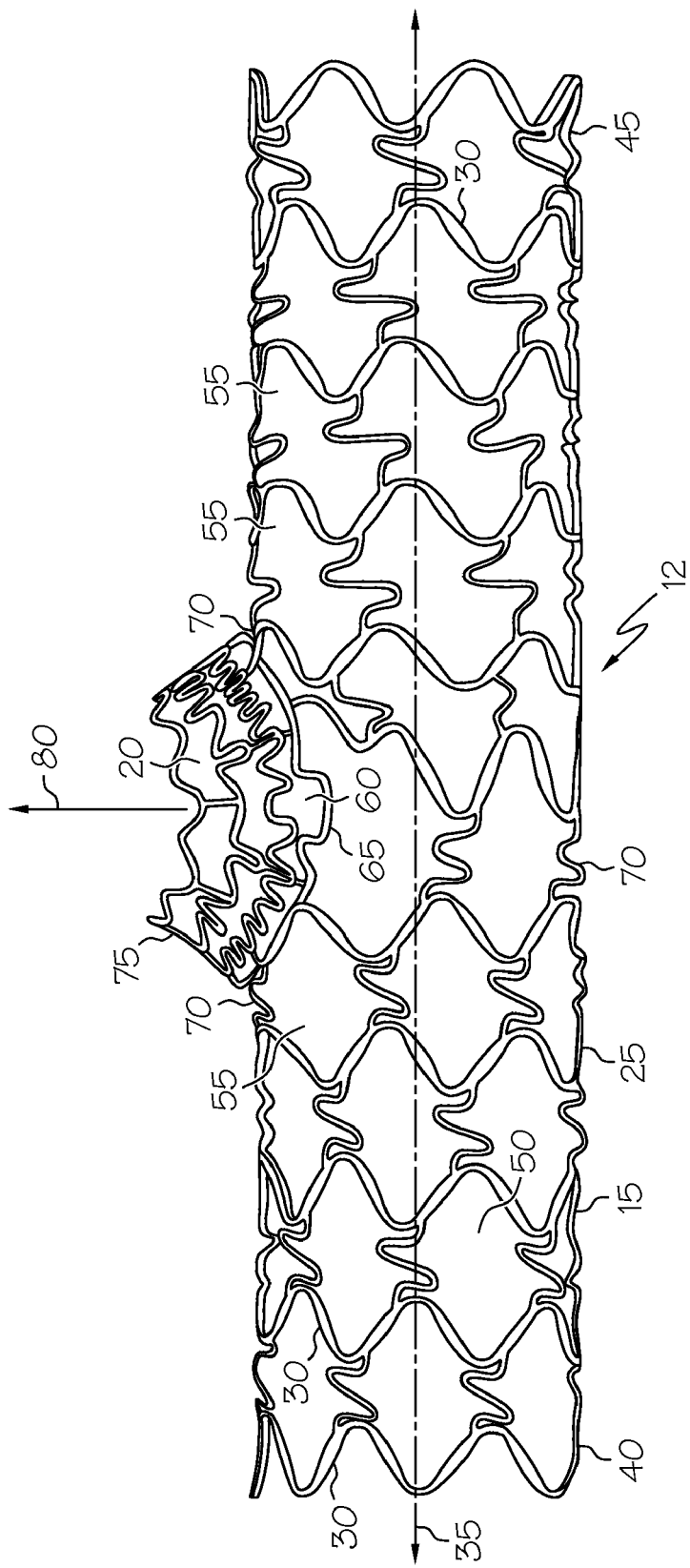
FIG. 1a is a side view of an embodiment of the present bifurcated stent.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

FIG. 1a depicts an embodiment of the invention, which includes a bifurcated stent with bioabsorbable members, wherein the stent 12 is shown in an expanded state.

In embodiments of the invention bioabsorbable members are constructed from one or more metals, polymers or combinations thereof that are corrodible so as to dissolve, dissociate or otherwise break down in the body without ill effect. Examples of such materials have been referred to as being degradable, biodegradable, biologically degradable, erodable, bioabsorbable, bioresorbable, and the like, and are herein collectively referred to as being bioabsorbable materials.

Examples of bioabsorbable materials include, but are not limited to, poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoesters, polyanhydrides, poly(glycolic acid), poly(D,L-lactic acid), poly(glycolic acid-co-trimethylene carbonate), polyphosphoesters, polyphosphoester urethanes, poly(amino acids), cyanoacrylates, poly(trimethylene carbonate), poly(iminocarbonate), copoly(ether-esters) (e.g. PEO/PLA), polyalkylene oxalates, polyphosphazenes and biomolecules such as fibrin, fibrinogen, cellulose, starch, collagen, hyaluronic acid, etc., and mixtures thereof. Further examples of bioabsorbable materials may be found in U.S. Pat. Nos. 6,258,117, 6,409,754, and 7,022,132 and in U.S. Patent Application Publication No. 2002/0107560, the entire contents of which are incorporated herein by reference.

As stated above, the stent comprises a main body 15 and a first branch 20. The main body 15 comprises a body wall 25 made up of interconnected stent members 30. As seen in FIG. 1a, the body wall 25 extends along a main longitudinal axis 35 from a proximal end 40 of the main body to a distal end 45 of the main body, defining a lumen 50 therethrough.

Regarding the interconnected stent members 30, the stent members 30 include struts, connectors, sutures, expansion joints, combinations thereof, or any number of other structures suitable for use in constructing a stent. A plurality of the interconnected stent members 30 define a plurality of cells 55. At least one of the cells 55 is a side opening 60. The side opening 60 is distinguishable because it is shaped differently then the other cells of the stent. In some embodiments, the side opening 60 is larger than the other cells. Additionally, the side opening 60 has a perimeter 65. One of ordinary skill in the art will recognize that the perimeter 65 can be any number of shapes and is not limited to circular, elliptical, or any of the shapes specifically depicted in the drawings.

Figure 1B:
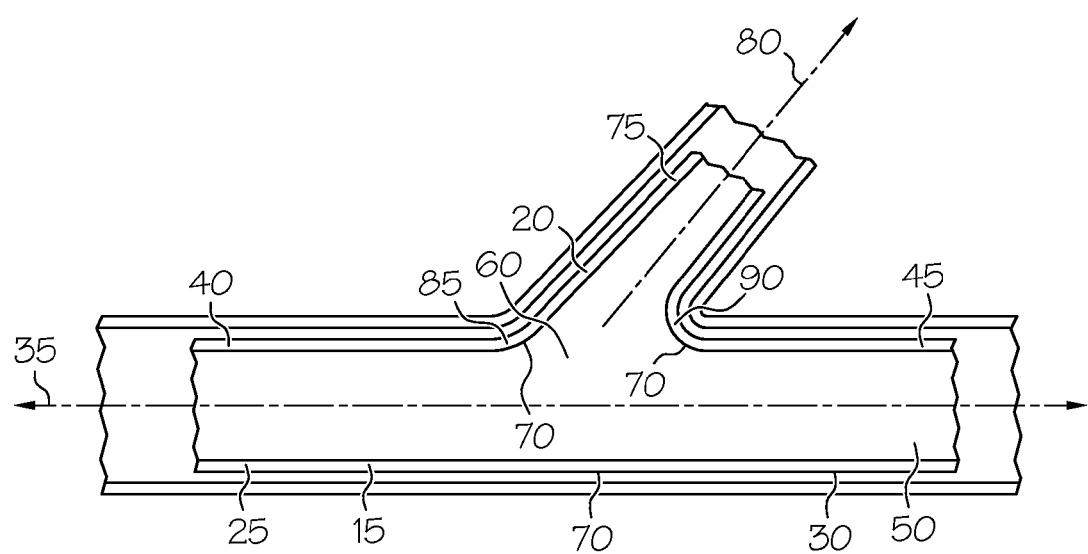

In addition to the main body, the stent further comprises a first branch 20 with a first branch body 75, as depicted in the embodiment shown in FIG. 1a. The first branch body 75 is positioned between the proximal end 40 and the distal end 45 of the main body 15. The first branch body 75 extends along a first branch longitudinal axis 80 when the stent is in the expanded state. As seen in FIG. 1a, the first branch body 75 extends from the body wall 25 from at least a first region 85 adjacent the side opening 60 and a second region 90 adjacent the side opening 60. At least one stent member adjacent the perimeter 65 is bioabsorbable. One or more bioabsorbable stent member(s) 70 is/are positioned anywhere on or within the structure of the stent 12. An example of embodiments including at least one bioabsorbable stent member 70, and the position of the member are shown in both FIG. 1a and in cross-sectional view FIG. 1b. The bioabsorbable stent member could be within the main body or within the first branch body.

The use of bioabsorbable stent members near or at the side opening is beneficial because it increases the stent's resistance to fatigue. When stents are juxtaposed or extended across a bifurcation in a vessel, for example, the juxtaposition or extension may stress areas of the stent. By placing bioabsorbable material at one or more of these high-stress areas, the bioabsorbable material will be gradually absorbed into the body, eliminating the stress. As a consequence of the absorption, the inventive stent will separate from itself, leaving in some embodiments the main body and the first branch body. Thus, the main vessel and the branch vessel will be kept open by the remaining portions of the stent. One skilled in the art will recognize that by selecting different bioabsorbable materials or varying the thickness of the bioabsorbable materials, the time it takes for the material to bioabsorb can be controlled. Thus in accordance with the present invention a bifurcated stent is provided wherein bioabsorbtion of a desired region or regions of the stent is made to occur immediately or soon after deployment, in several months, in several years, or at different rates for different regions of the stent.

Figure 2A:
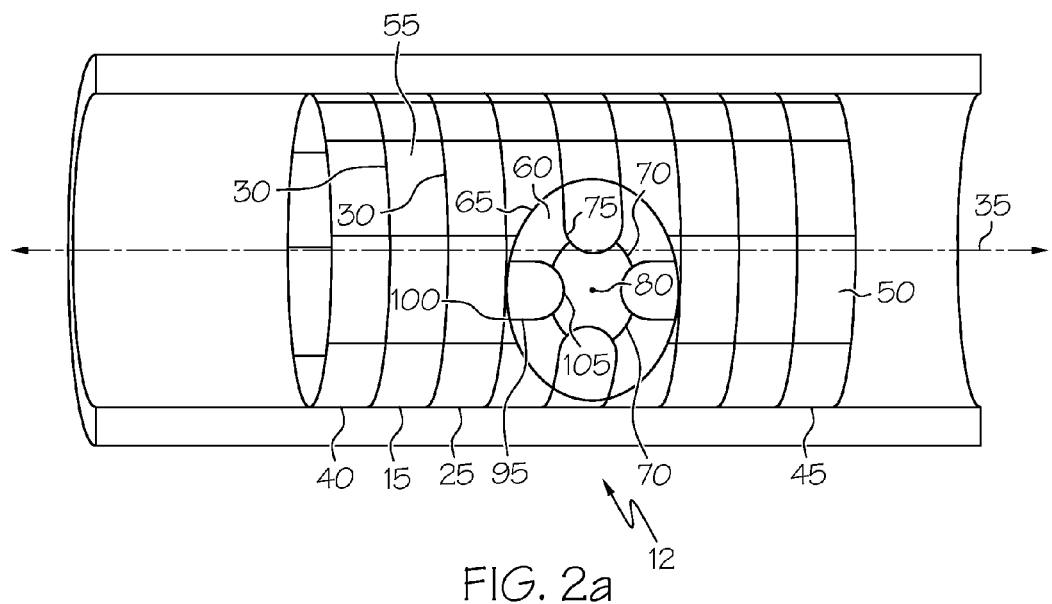
FIG. 2a is a perspective view of an embodiment of the inventive stent, with the deflectable members connected by bioabsorbable stent members.
Figure 2B:
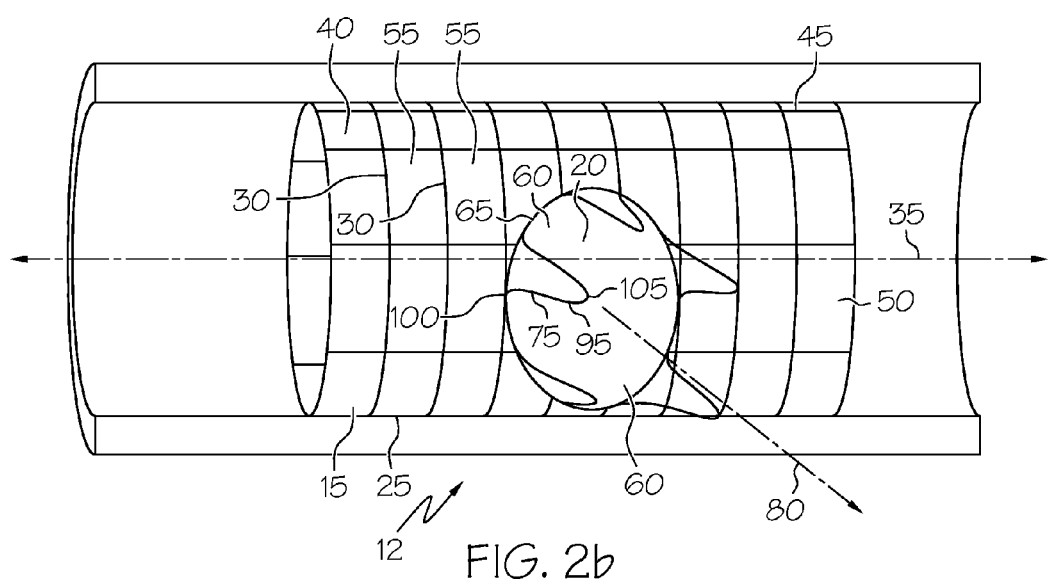
FIG. 2b is a perspective view of the embodiment shown in FIG. 2a, after the bioabsorbable stent members have degraded.

In some embodiments of the present invention, the first branch body comprises a plurality of deflectable members 95, as illustrated in side-view FIGS. 2a and 2b. These deflectable members 95 may define undulating petals, similar to those shown and described in U.S. Patent Application Publication Nos. 2004/0138737 and 2005/0102023, the entire contents of each being incorporated herein by reference. Each of the deflectable members 95 has a first end 100 and a second end 105. As shown in FIG. 2a, the first end 100 of each deflectable member 95 extends from the main body 15 at positions about the perimeter 65 of the side opening. In the expanded state, depicted in FIG. 2b, the deflectable members 95 extend into the branch vessel. One of ordinary skill in the art will recognize that there are a number of ways in which the deflectable members 95 may be deflected, including inserting an expandable balloon through the main body of the stent and through the side opening (not depicted). FIG. 2a shows the second ends 105 of adjacent deflectable members 95 being connected by at least one bioabsorbable stent member 70. In some embodiments it may be desirable to have the bioabsorbable connectors degrade upon stent deployment, such as depicted in FIG. 2b, which shows the deflectable members 95 after the bioabsorbable stent members have degraded.

Figure 3A:
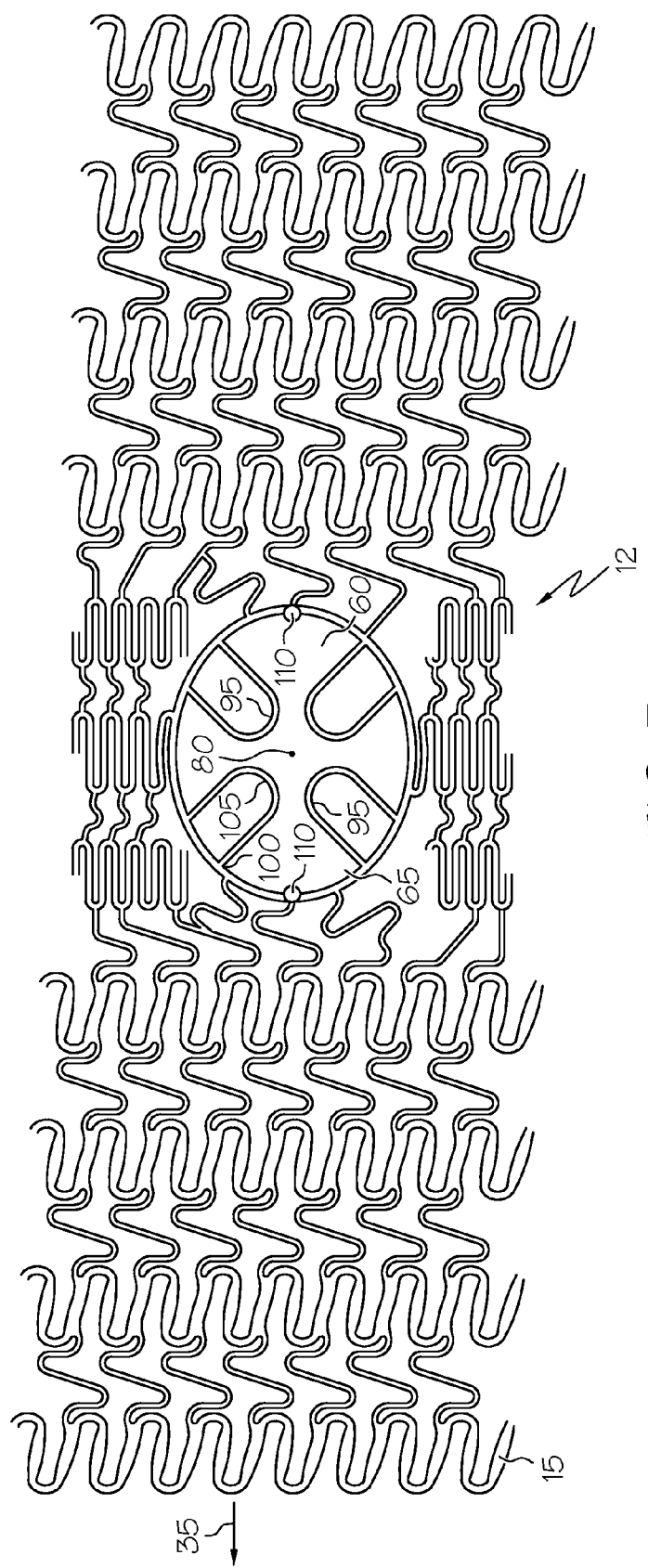
FIG. 3a is a flat layout of an embodiment of the inventive stent, with bioabsorbable expansion joints.
Figure 3B:
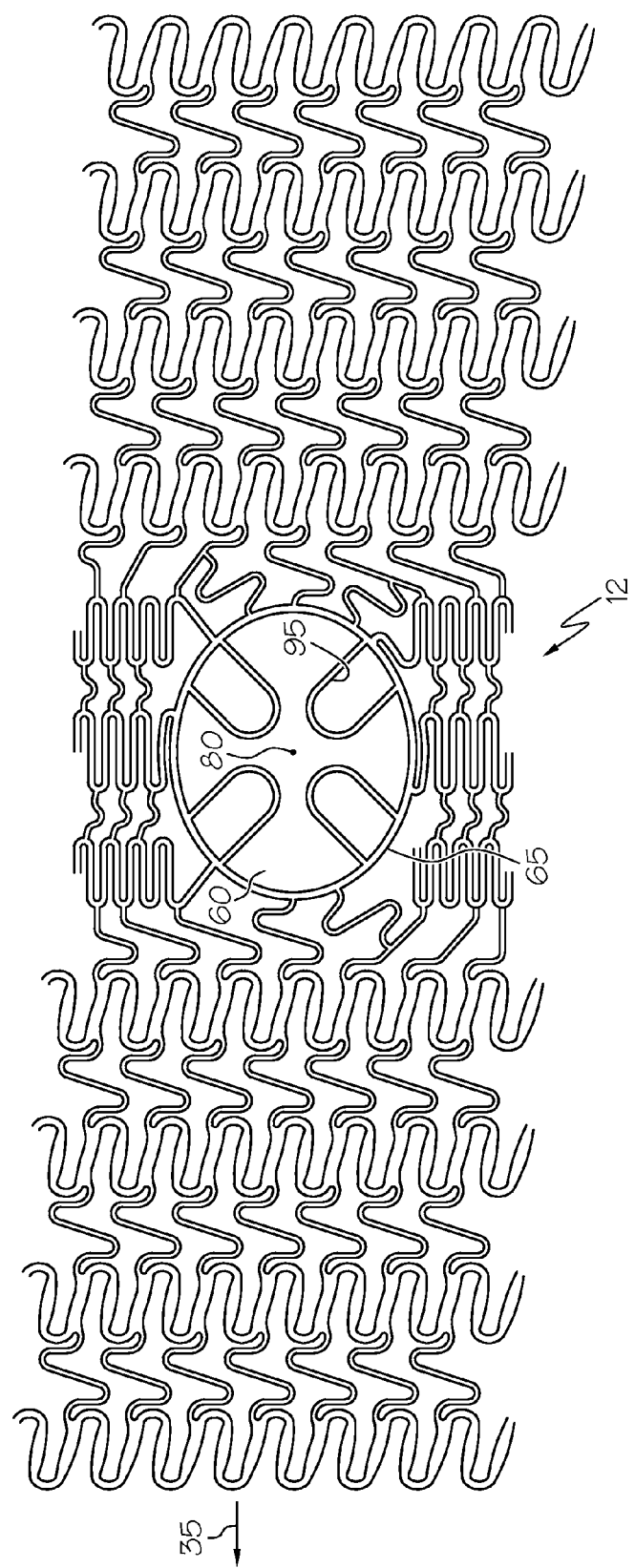
FIG. 3b is a flat layout of the embodiment depicted in FIG. 3a, after the bioabsorbable expansion joint has degraded.

In FIG. 3a, the embodiment of the stent depicted in FIG. 2a further includes a bioabsorbable expansion joint 110. Specifically, the perimeter 65 of the side opening 60 includes the bioabsorbable expansion joint 110. Including at least one bioabsorbable expansion joint allows the side opening to expand over time, reducing the stress on the perimeter. FIG. 3b depicts the stent of FIG. 3a after the bioabsorbable expansion joint 110 has degraded. This degradation eliminates the stress on the perimeter by allowing the perimeter to expand.

Figure 4A:
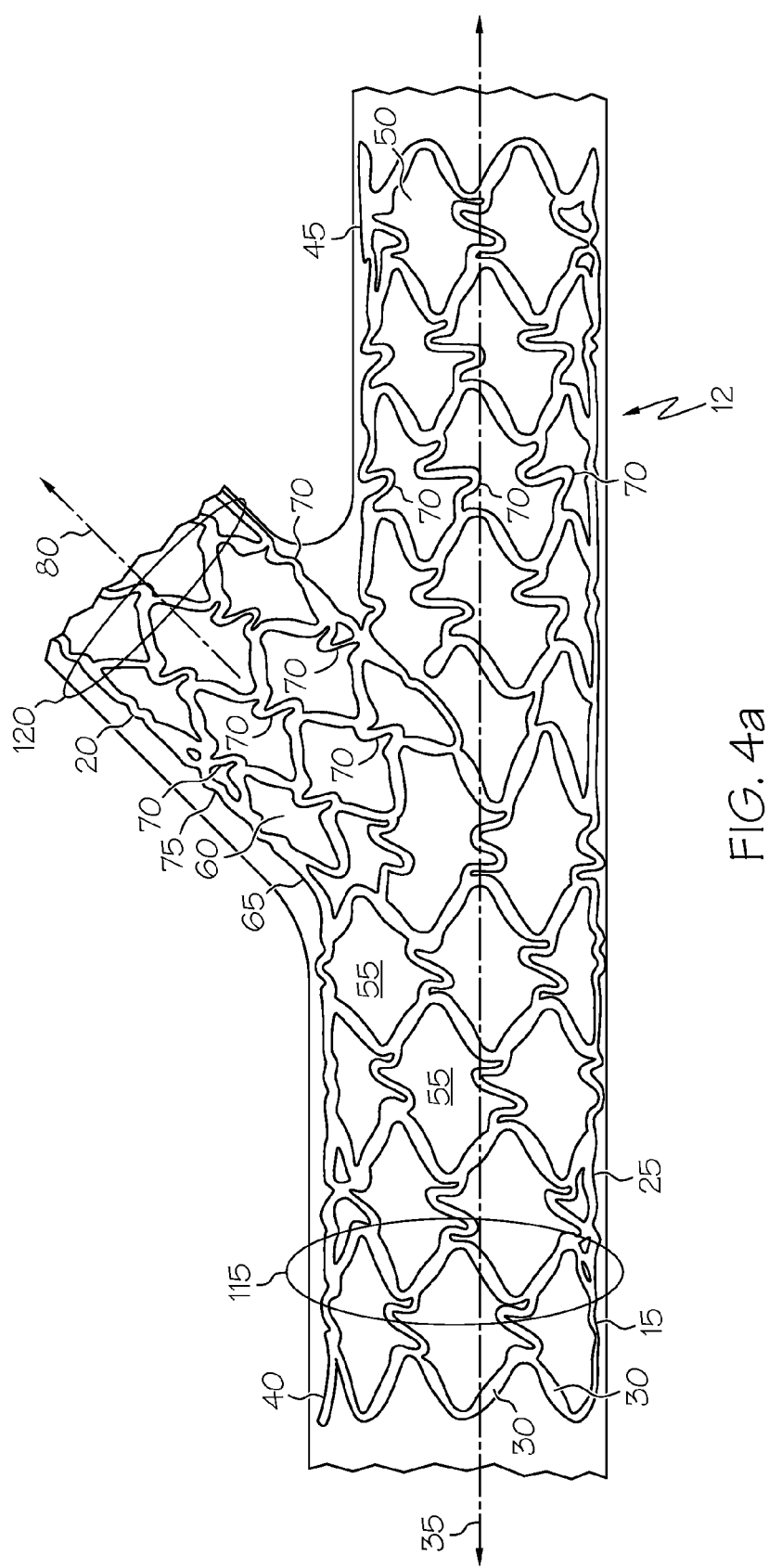
FIG. 4a is a side view of an embodiment of the inventive stent, with circumferential rings in the main body and branch rings in the branch body.
Figure 4B:
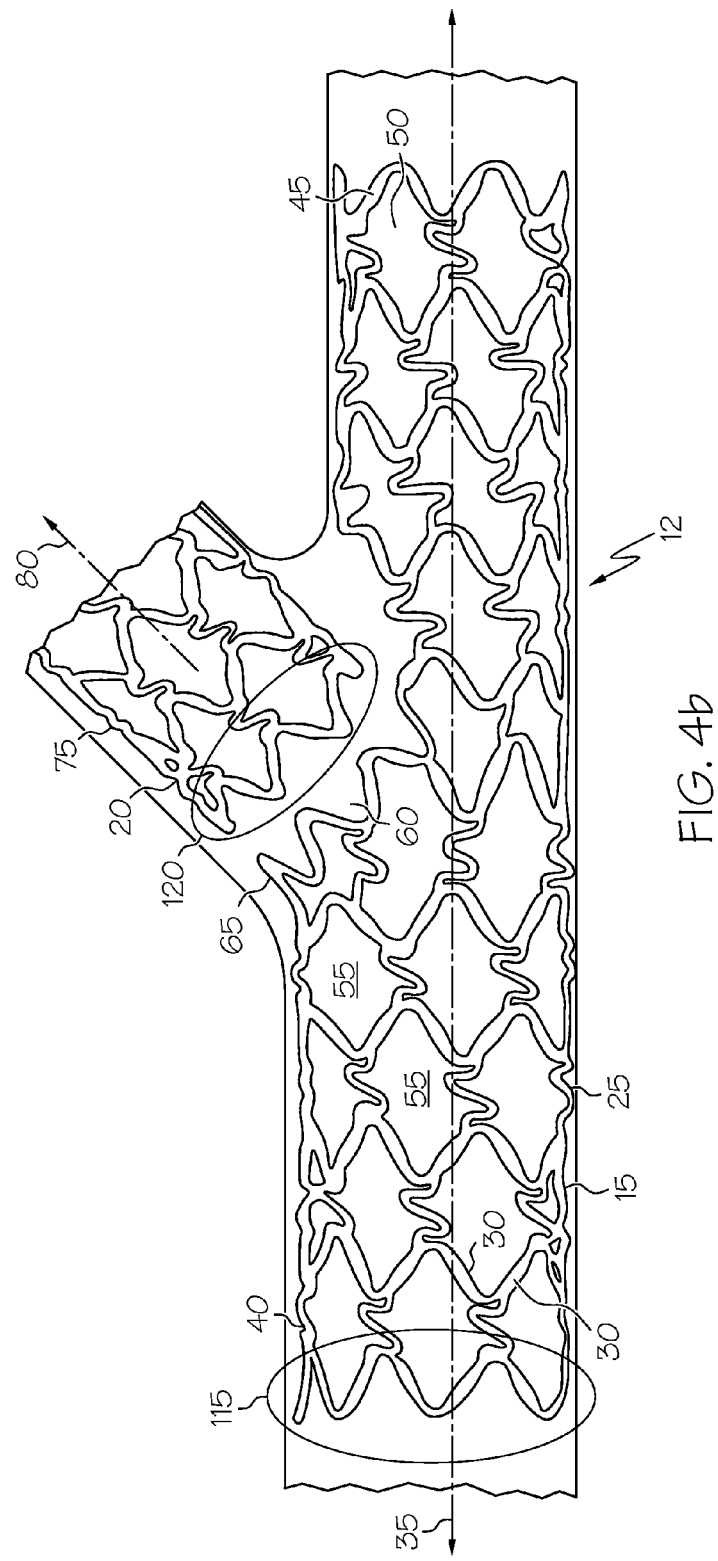
FIG. 4b is a side view of the embodiment depicted in FIG. 4a, after the bioabsorbable stent members have degraded.

Referring now to FIG. 4a, in the embodiment shown, the body wall 25 comprises a plurality of circumferential rings 115 longitudinally offset from one another about the main longitudinal axis 35. In FIG. 4a, the first branch body 75 shown comprises at least one branch ring 120 arranged about the first branch axis 80. The branch ring 120 extends from the perimeter 65 of the side opening by at least one bioabsorbable stent member 70. After the bioabsorbable stent members degrade, the branch body 75 separates from the perimeter 65, as illustrated in FIG. 4b.

Figure 4C:
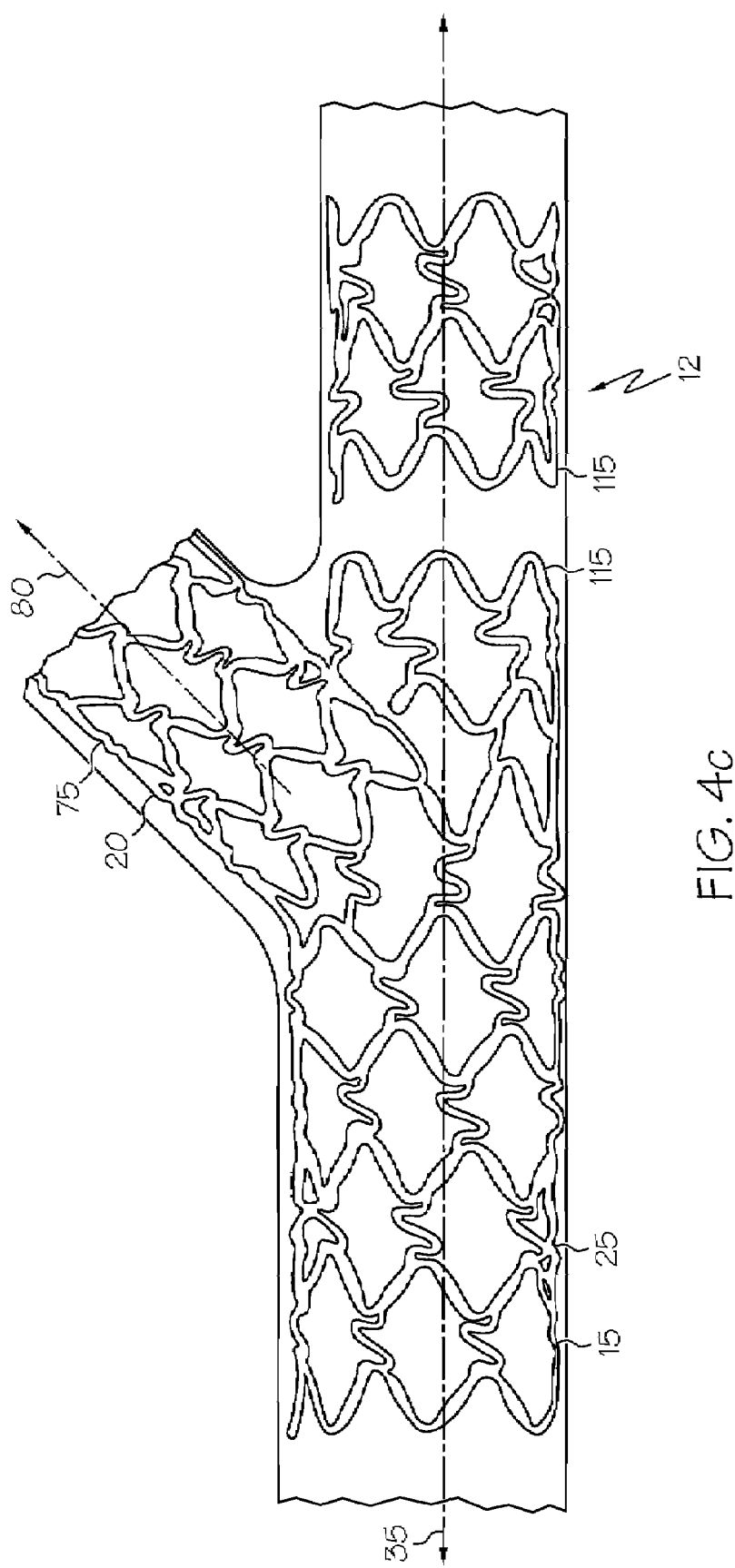
FIG. 4c is a side view of the embodiment depicted in FIG. 4a, after the bioabsorbable stent members have degraded.

In the embodiment depicted in FIG. 4a, adjacent circumferential rings 115 are also connected to one another by bioabsorbable stent members 70. As illustrated in FIG. 4c, this allows at least a portion of the main body 25 to separate.

Figure 4D:
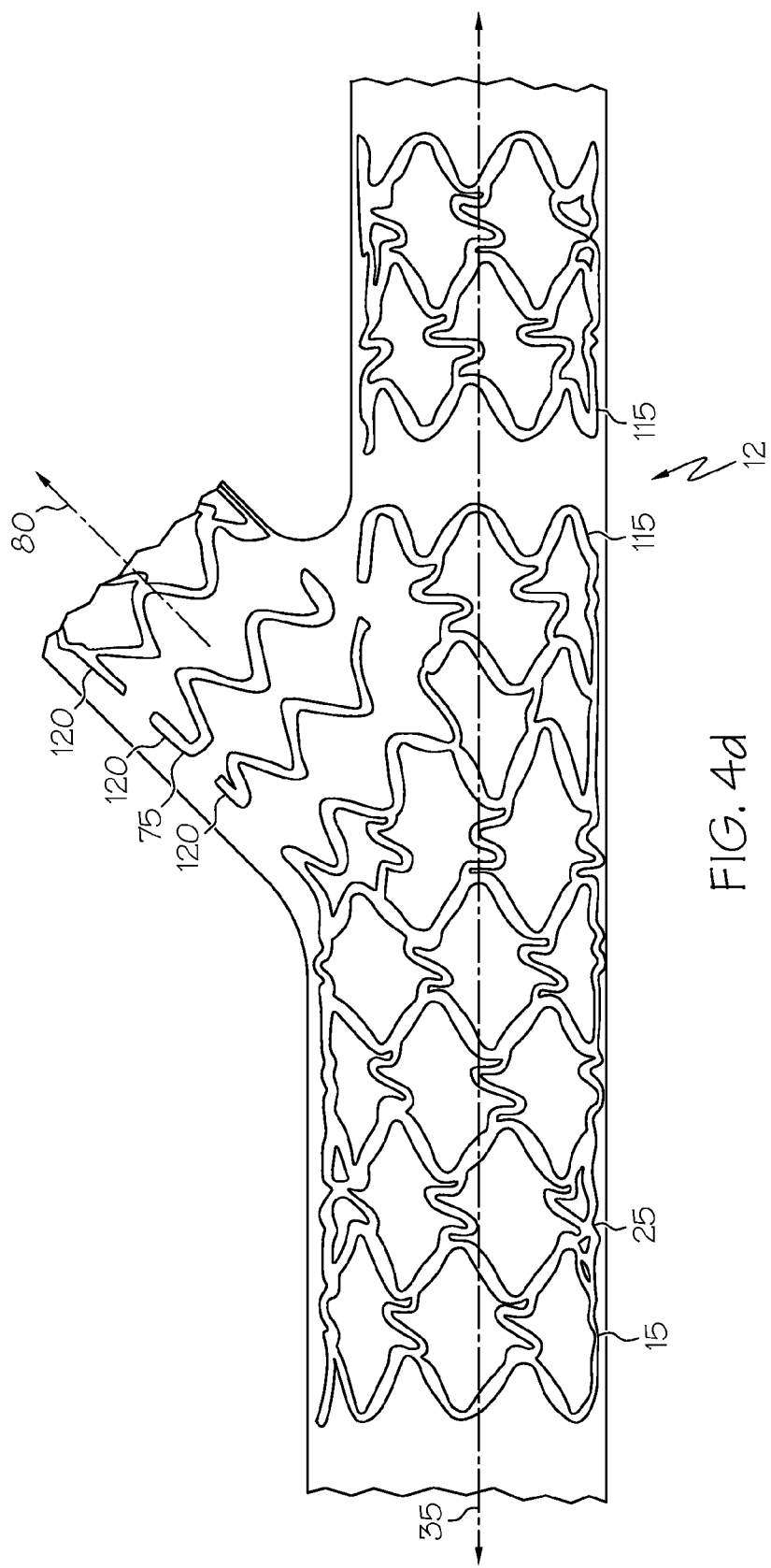
FIG. 4d is a side view of the embodiment depicted in FIG. 4a, after the bioabsorbable stent members have degraded.

In some embodiments, as also depicted in FIG. 4a, the stent comprises a plurality of branch rings 120. Adjacent branch rings 120 are connected to one another by at least one bioabsorbable stent member 70. As illustrated in FIG. 4d, this allows at least a portion of the branch body 75 to separate, leaving multiple branch rings after the bioabsorbable stent member(s) degrade.

Figure 5A:
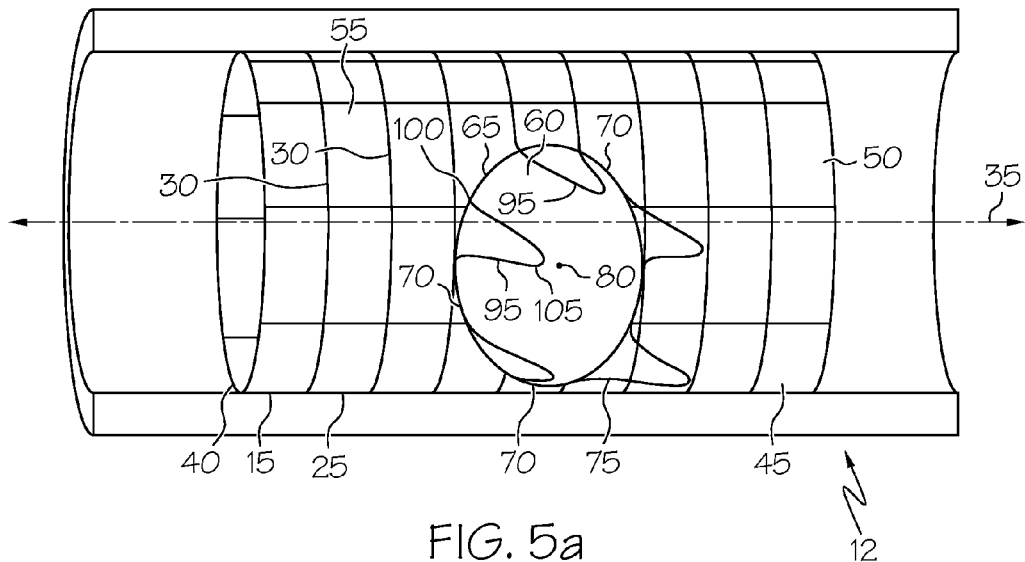
FIG. 5a is a perspective view of an embodiment of the inventive stent, with the deflectable members extending from a bioabsorbable perimeter.
Figure 5B:
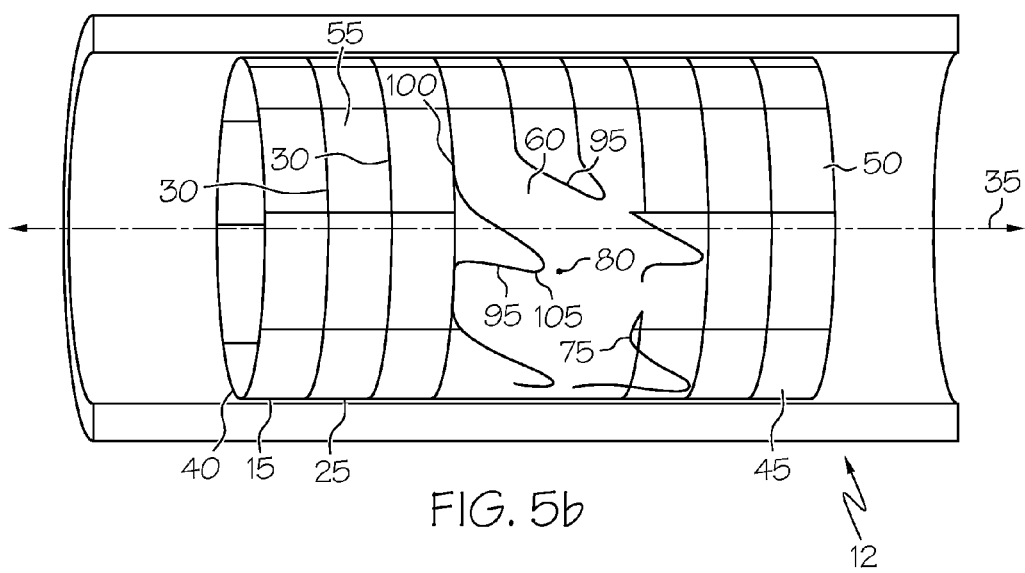
FIG. 5b is a perspective view of the embodiment shown in FIG. 5a, after the bioabsorbable perimeter has degraded.

In the embodiment depicted in FIG. 5a, the perimeter 65 is made up of at least one bioabsorbable stent member 70. The stent further comprises a plurality of deflectable members 95, each having a first end 100 and a second end 105. Provision of the bioabsorbable perimeter mitigates fracturing between the main body and the deflectable members. The first end 100 of each deflectable member 95 extends from the main body 15 at positions about the perimeter 65 of the side opening. In the expanded state, as shown in FIG. 5a, the deflectable members 95 extend into a vessel branch. FIG. 5b depicts the stent 12 of FIG. 5a after the bioabsorbable stent member(s) 70 of the perimeter has degraded. As seen in FIG. 5b, the deflectable members 95 are separated from the main body 15 after the perimeter 65 has degraded.

Figure 6A:
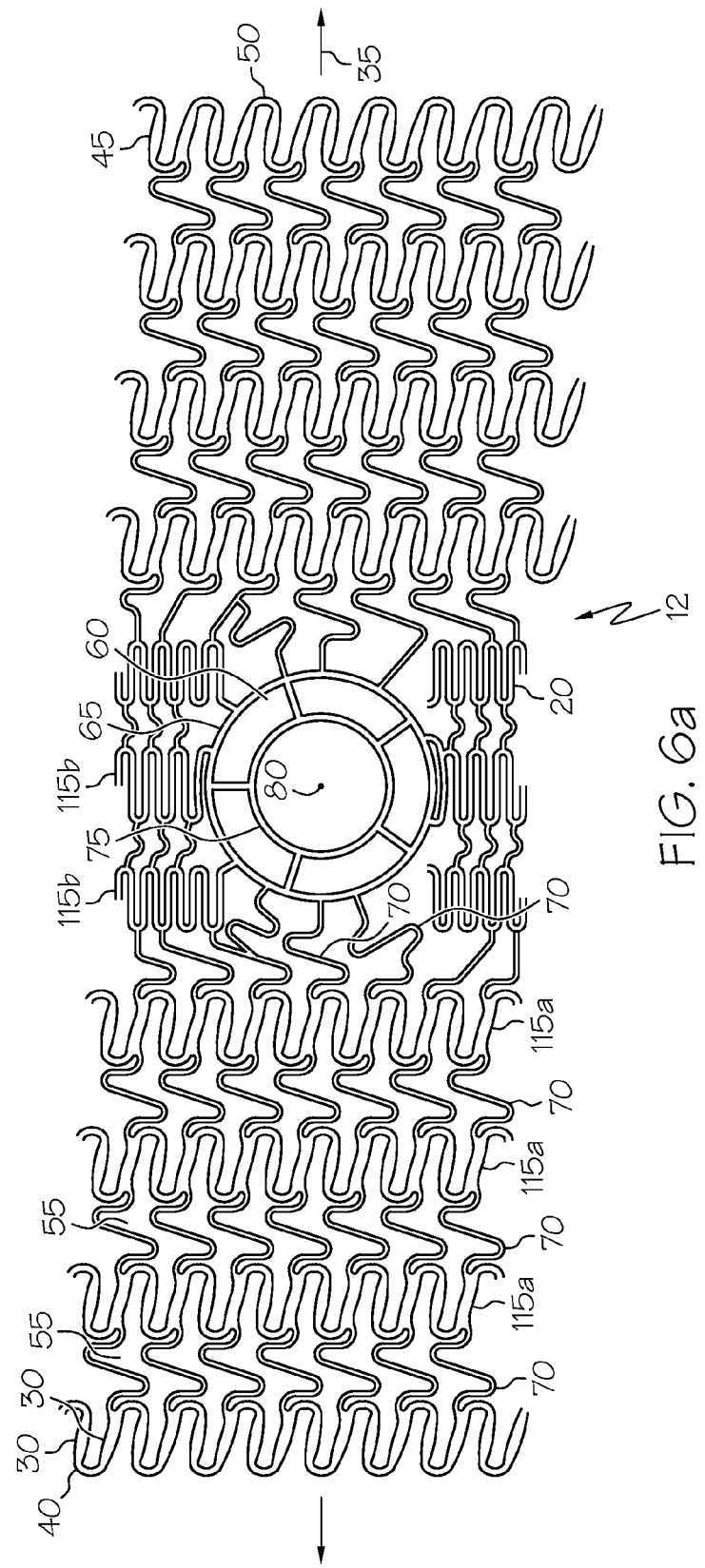
FIG. 6a is a flat layout of an embodiment of the inventive stent, with circumferential rings adjacent the side opening engaged to the side opening by bioabsorbable stent members.

In some embodiments, as depicted in FIG. 6a, the body wall 25 comprises a plurality of circumferential rings 115a being longitudinally offset from one another about the main longitudinal axis 35. As illustrated, at least two adjacent circumferential rings 115a are connected to one another by at least one bioabsorbable stent member 70. Also, at least one of the circumferential rings 115a adjacent the perimeter 65 is connected to the perimeter 65 by at least one bioabsorbable stent member 70. In some embodiments, the stent includes deflectable members 95, like in FIG. 6b.

Figure 6B:
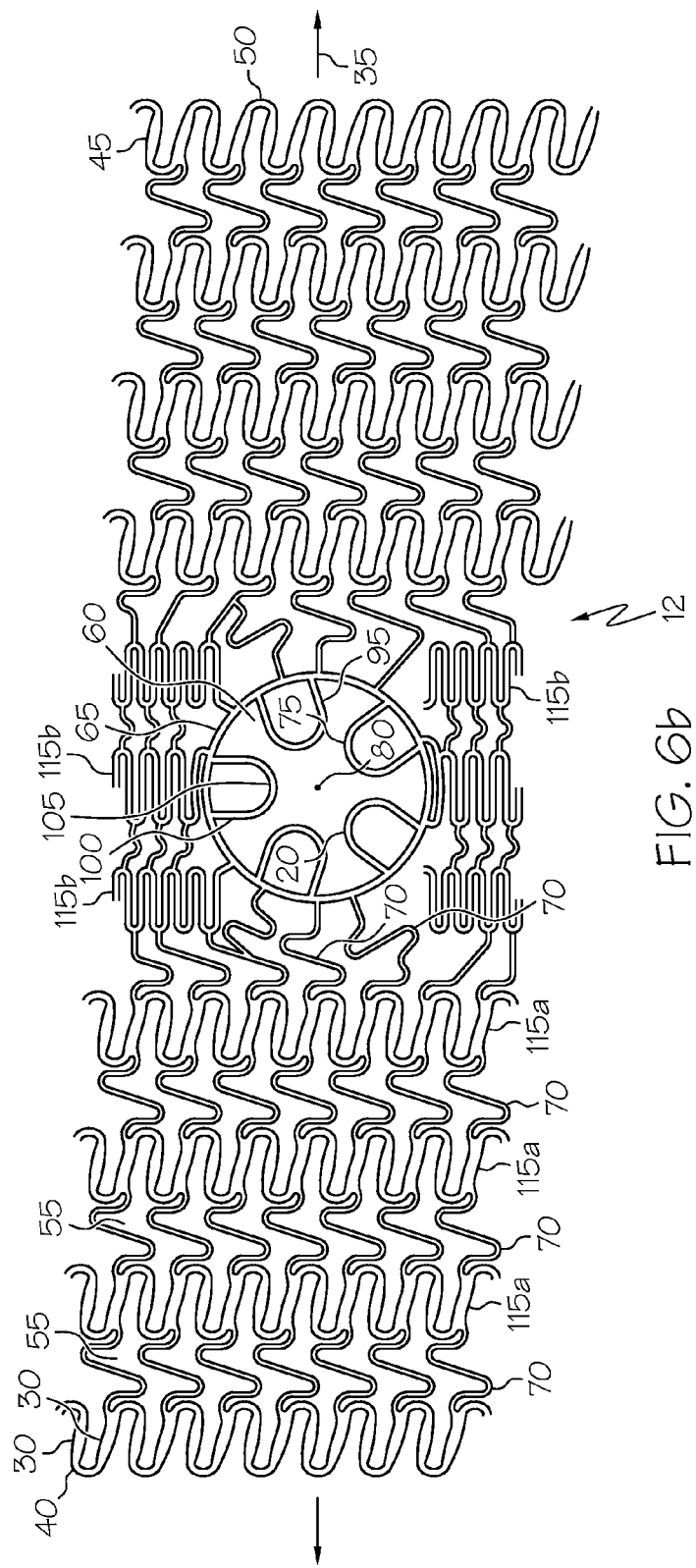
FIG. 6b is a flat layout of the embodiment depicted in FIG. 6a with deflectable members.

In at least one embodiment, as shown in FIG. 6a, the stent further comprises at least one circumferential ring 115b engaged to the perimeter 65. One of the circumferential rings 115a adjacent and connected to the perimeter 65 by at least one bioabsorbable stent member 70 is also connected by at least one bioabsorbable stent member 70 to a circumferential ring 115b engaged to the perimeter 65. The stent further comprises a plurality of deflectable members 95 having a first end 100 and a second end 105, as shown in FIG. 6b. The first end 100 of each deflectable member 95 extends from the main body at positions about the perimeter 65.

Figure 7A:
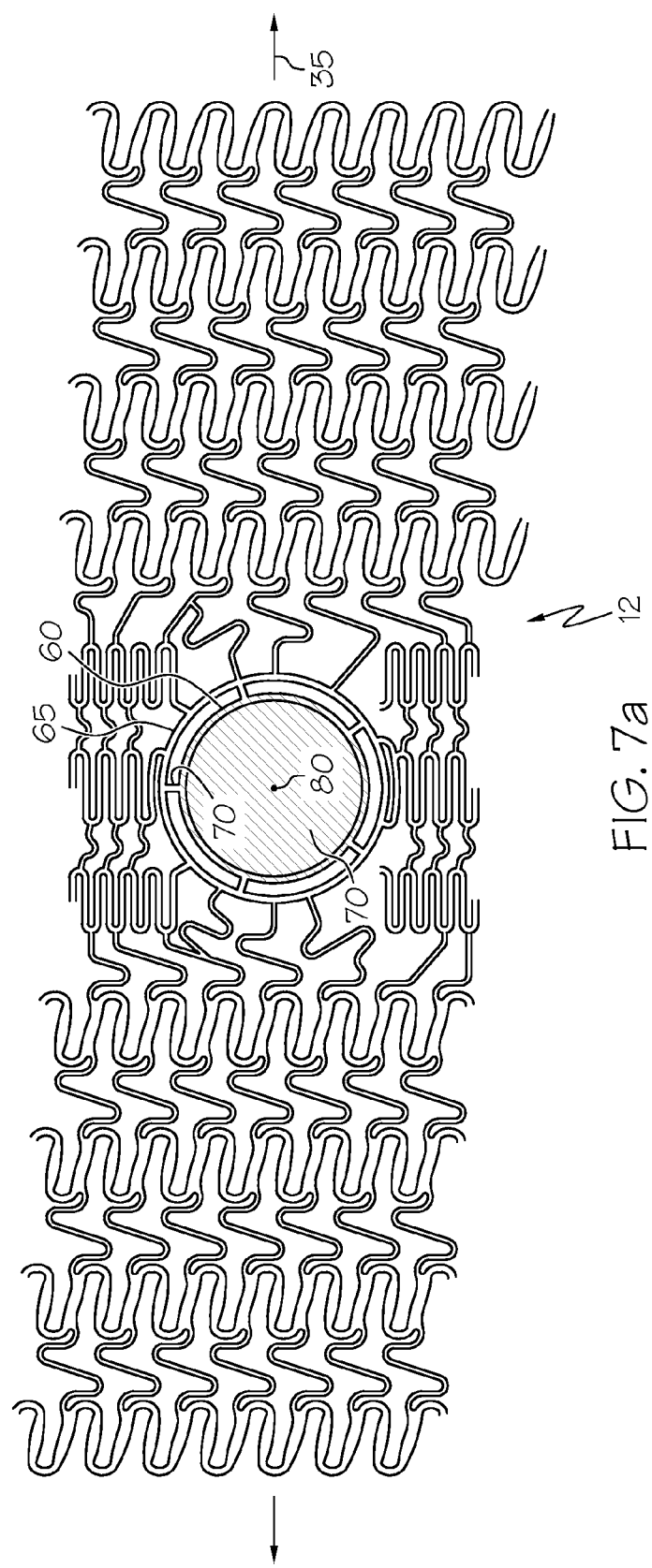
FIG. 7a is a flat layout of an embodiment of the inventive stent, with a bioabsorbable stent member substantially covering the side opening.
Figure 7B:
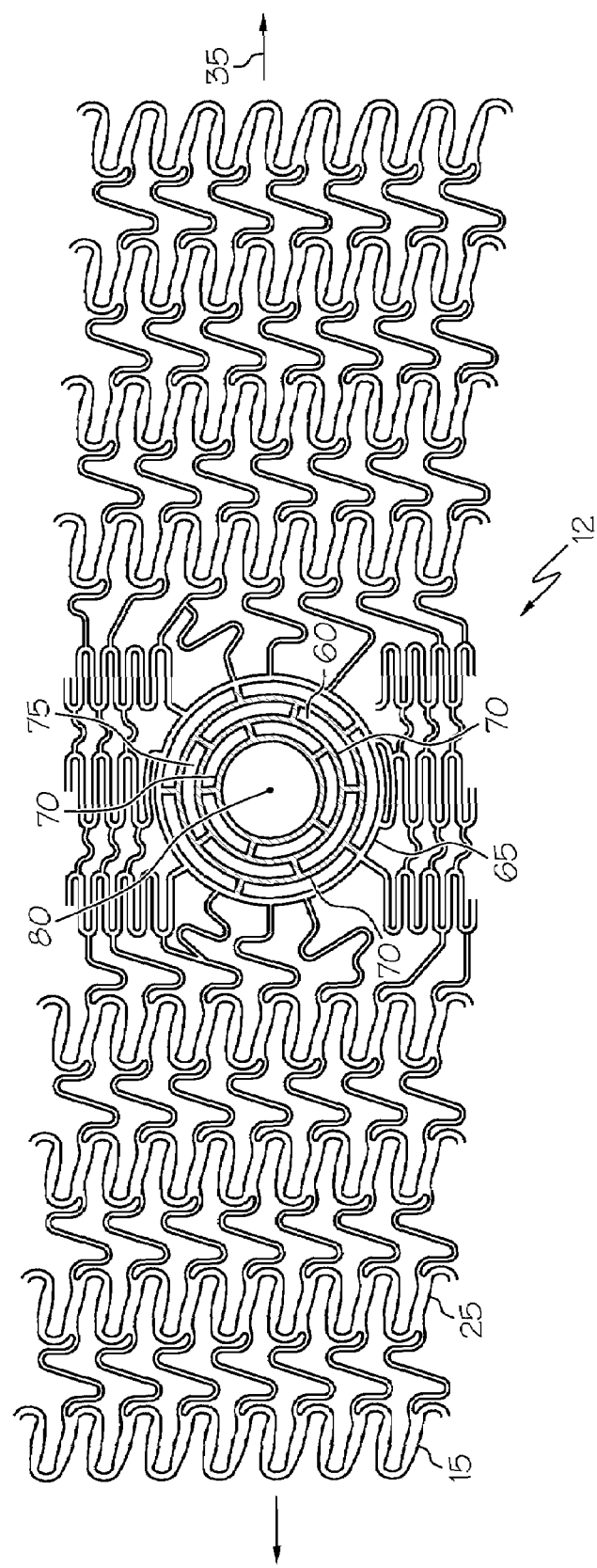
FIG. 7b is a flat layout of an embodiment of the inventive stent, with a plurality of bioabsorbable stent members substantially covering the side opening.

Referring now to FIG. 7a, in at least one embodiment, at least one bioabsorbable stent member 70 substantially covers the side opening 60. As seen in FIG. 7a, the covering extends from the perimeter 65. In some embodiments, the covering is engaged to the perimeter by other bioabsorbable stent members 70, as in FIG. 7a. In another embodiment, the covering extends directly from the perimeter 65. In some embodiments, as shown in FIG. 7b, a plurality of bioabsorbable stent members 70 substantially covers the side opening 60. Although depicted as concentric circles, it should be noted that the bioabsorbable stent members 70 could be arranged in any number of designs to cover the side opening 60.

It should be noted that in the unexpanded state, the first branch body 75 would lie flat on the main body 15. The first branch body 75 could be expanded into a second lumen with a secondary balloon attached to the main balloon, a POBA balloon pushed through the center of the first branch body 75 and expanded, or a secondary deployment object such as a conic-shaped feature at the end of a catheter could be extended through first branch body 75 to push it open.

Referring now to the embodiment depicted in FIG. 7b, the first branch body 75, shown with ring-like stent members 70, could be expanded into a second lumen by a ratcheting procedure. One of ordinary skill in the art will recognize that there are a number of ways in which the ratcheting can be performed. One ratcheting method would be similar to that of zip ties, which allows the rings to open, but prevents the ring from closing. In some embodiments, the ring-like stent members 70 have elastic properties that allow them to stretch open, at which point the ring-like stent members 70 either separate as they expand, or depending on the taper of the second lumen, the ring-like stent members 70 are pushed into the second lumen, resulting in a conical shape.

Figure 8A:
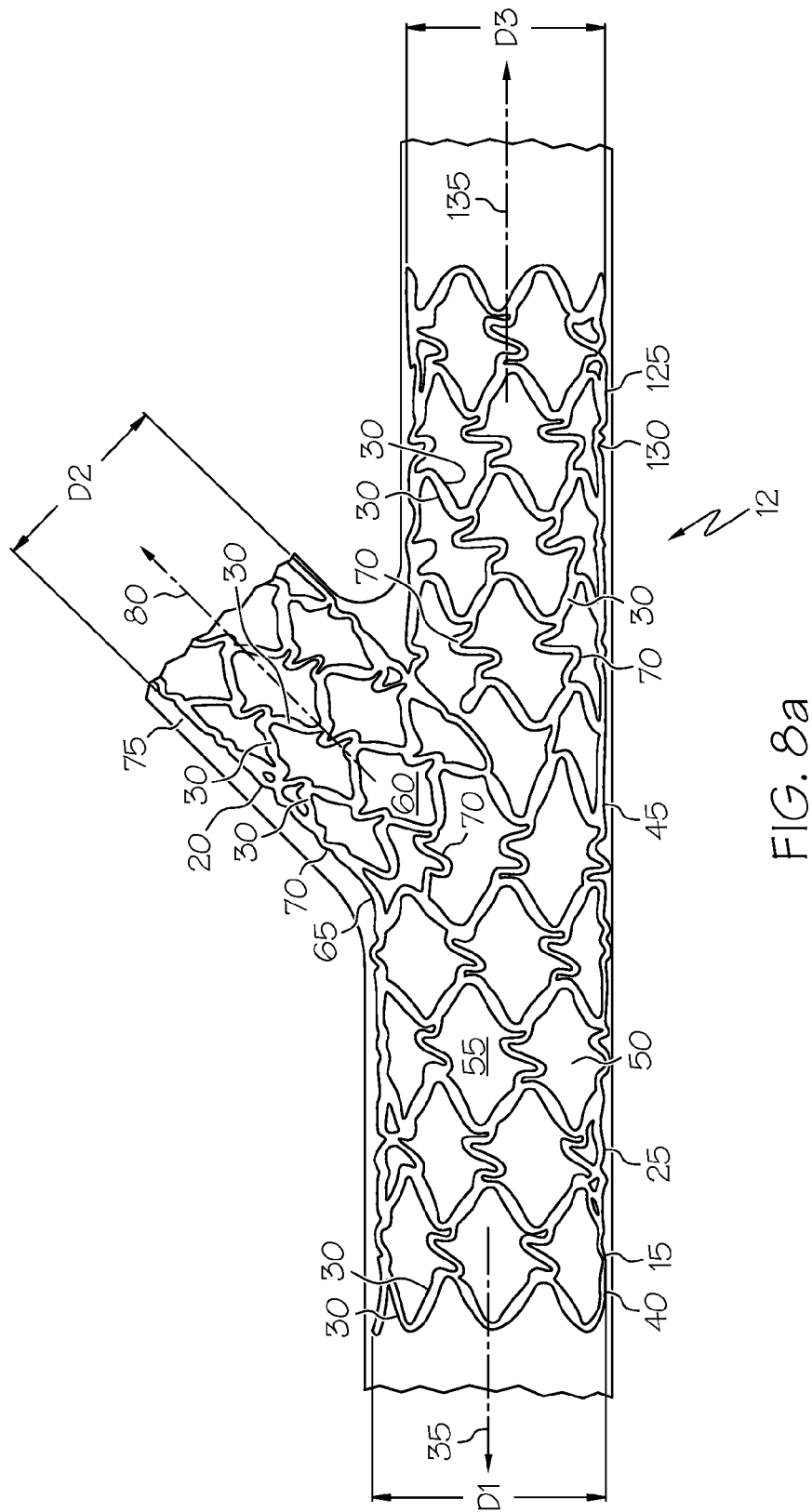
FIG. 8a is a side view of an embodiment of the inventive stent, with two branches extending from the distal end of the main body by bioabsorbable stent members.

In the embodiment depicted in FIG. 8a, a Y-stent is depicted. The stent 12 in FIG. 8a comprises a main body 15 and two branches (20, 125). The main body 15 has a body wall 25 which extends along a main longitudinal axis 35 from a proximal end 40 to a distal end 45 and defines a lumen 50 therethrough. The body wall 25 is comprised of interconnected stent members 30.

As mentioned above, the bifurcated stent of FIG. 8a has two branches, a first branch 20 and a second branch 125. The first branch 20 has a first branch body 75 which extends along a first branch longitudinal axis 80 when the stent 12 is in the expanded state, as in FIG. 8a. Like the main body, the first branch body 75 is comprised of interconnected stent members 30.

The second branch 125 of stent 12 has a second branch body 130 which extends along a second branch longitudinal axis 135 when the stent 12 is in the expanded state. The second branch body 130 is also comprised of interconnected stent members 30.

Figure 8B:
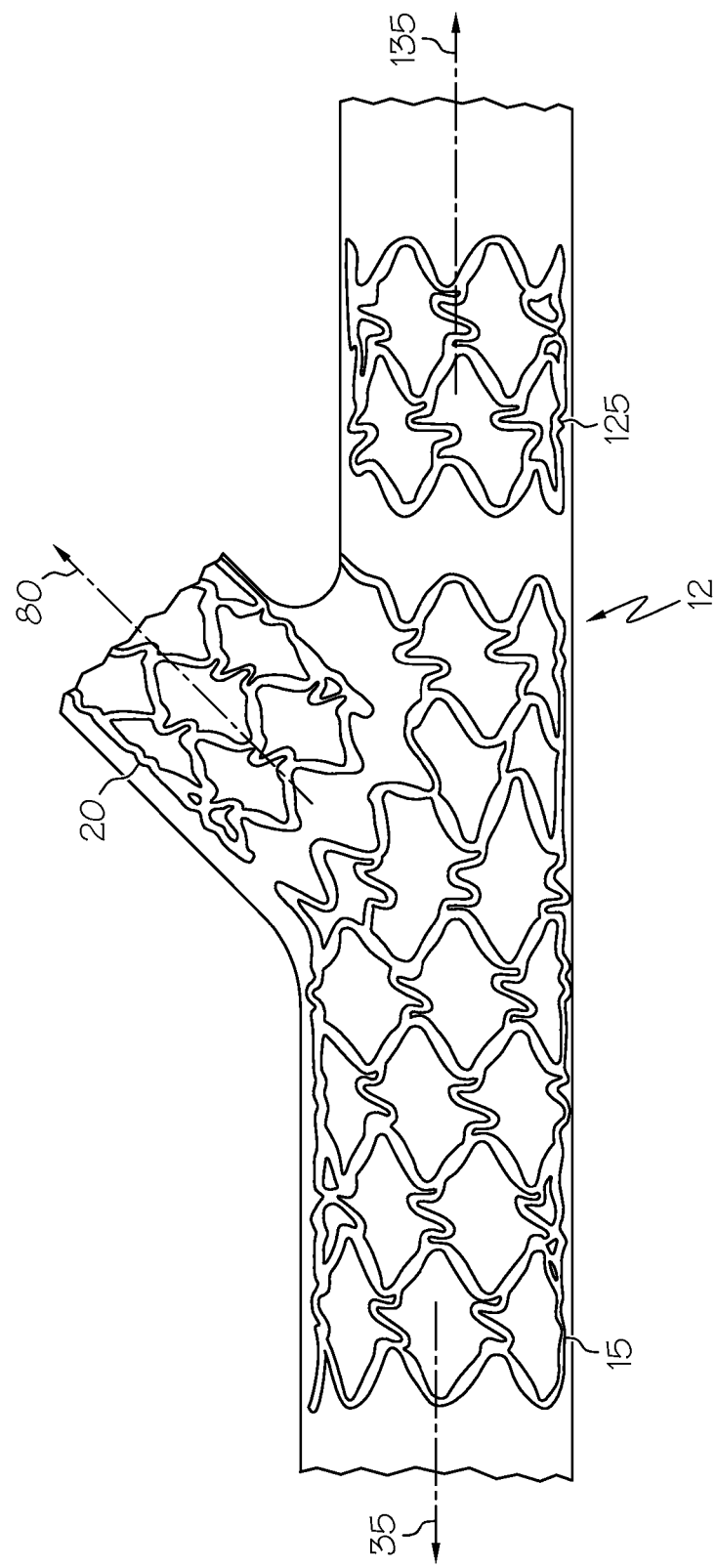
FIG. 8b is a side view of the embodiment depicted in FIG. 8a, after the bioabsorbable stent members have degraded.

As seen in FIG. 8a, the first and second branch bodies 75, 130 extend from the main body 15 at its distal end 45. Furthermore, at least one of the stent members 30 of the first branch body 75 and the second branch body 130 are connected to the main body 15 at the distal end 45 by at least one bioabsorbable stent member 70. FIG. 8b depicts the stent 12 of FIG. 8a after the bioabsorbable stent members 70 have degraded. The first branch 20 and the second branch 125 have separated from the main body 15.

It should be noted that the terms "main body", "first branch", and "second branch" do not imply that the diameter of the main branch is larger than the diameters of the first or second branches. Although this could be true, it is not necessarily so. In some embodiments, the diameter of the first branch D2 or the diameter of the second branch D3 is equal to or greater than the main branch diameter D1.

Figure 9:
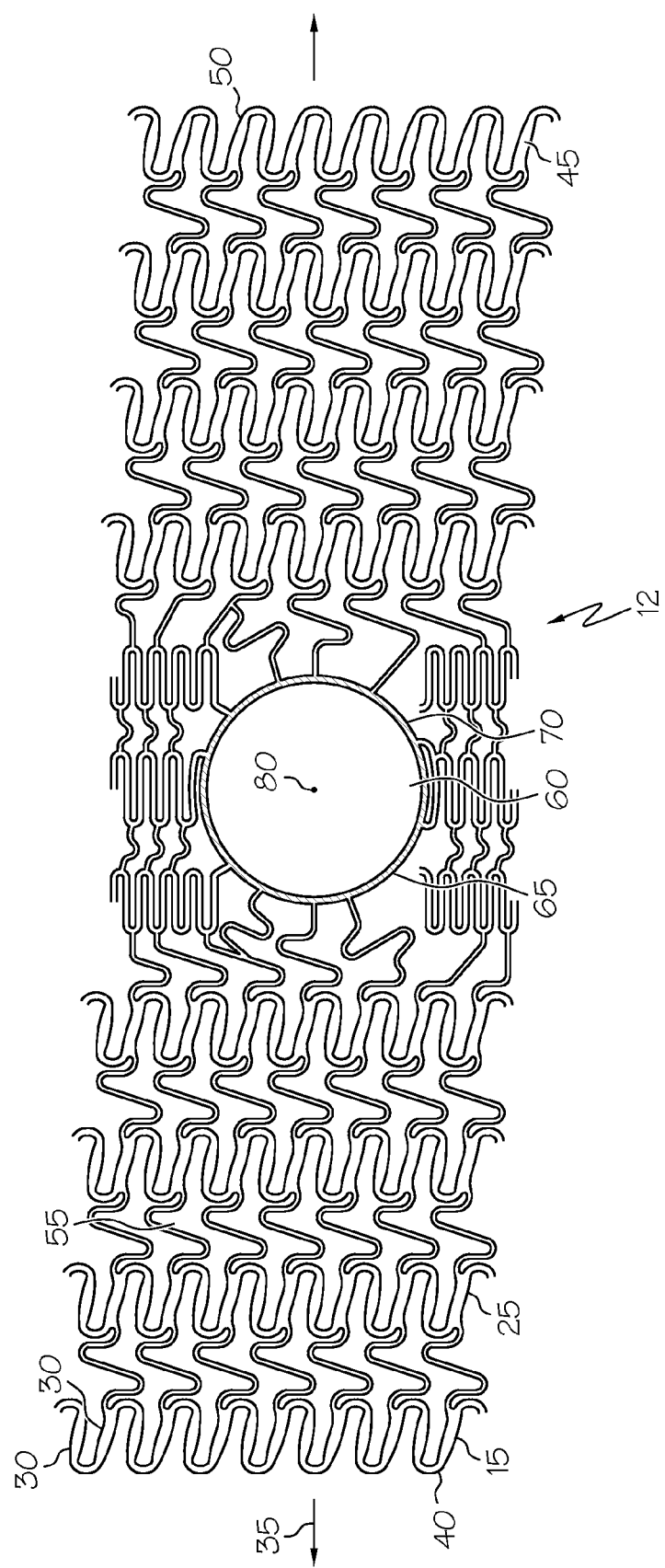
FIG. 9 is a flat layout of an embodiment of the inventive stent, with a bioabsorbable perimeter.

Referring now to FIG. 9, in at least one embodiment the expandable stent 12 has a main body 15 with a body wall 25 which extends along a main longitudinal axis 35 from a proximal end 40 to a distal end 45 and defining a lumen 50 therethrough.

As in other embodiments described above, the body wall 25 is comprised of interconnected stent members 30, a plurality of which define a plurality of cells 55. At least one of the cells 55 is a side opening 60. The side opening 60 is distinguishable because it is shaped differently then the other cells of the stent. In general, the side opening 60 is shaped differently than the other cells in that it is larger than the other cells. Additionally, the side opening 60 has a perimeter 65. In the embodiment depicted in FIG. 9, the perimeter 65 is bioabsorbable.

In some embodiments, the stent may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A bifurcated stent, the stent having an unexpanded state and an expanded state, the stent comprising:
   a main body with a body wall, the body wall extending along a main longitudinal axis from a proximal end to a distal end and defining a lumen therethrough, the body wall comprised of interconnected stent members, a plurality of the interconnected stent members defining a plurality of cells, at least one of the plurality of cells being a side opening, the side opening being shaped differently then the other cells of the stent, the side opening having a perimeter; and
   a first branch having a first branch body, the first branch body comprised of interconnected stent members, the first branch body positioned between the proximal end and the distal end of the main body, the first branch body extending along a first branch longitudinal axis when the stent is in the expanded state, the first branch body extending from the body wall from at least a first region adjacent the side opening and a second region adjacent the side opening; and
   at least one stent member adjacent the perimeter being bioabsorbable, wherein the at least one bioabsorbable stent member substantially covers the side opening.

2. The stent of claim 1, wherein the first branch body comprises a plurality of deflectable members, each of the deflectable members having a first end and a second end, the first end of each deflectable member extending from the main body at positions about the perimeter of the side opening, the second ends of adjacent deflectable members being connected by at least one bioabsorbable stent member.

3. The stent of claim 2, wherein the perimeter of the side opening comprises at least one bioabsorbable expansion joint.

4. The stent of claim 1, wherein the body wall comprises a plurality of circumferential rings, the plurality of rings being longitudinally offset from one another about the main longitudinal axis, and wherein
   the first branch body comprises at least one branch ring, the branch ring being arranged about the first branch axis, the at least one branch ring extending from the perimeter of the side opening by at least one bioabsorbable stent member.

5. The stent of claim 4, wherein adjacent circumferential rings are connected to one another by at least one bioabsorbable stent member.

6. The stent of claim 4, further comprising a plurality of branch rings, adjacent branch rings being connected to one another by at least one bioabsorbable stent member.

7. The stent of claim 4, wherein the at least one bioabsorbable stent member is a suture.

8. The stent of claim 7, wherein at least two adjacent circumferential rings of the main body are connected by at least one bioabsorbable stent member.

9. The stent of claim 1, wherein at least a portion of the perimeter is bioabsorbable, the stent further comprising a plurality of deflectable members, each deflectable member having a first end and a second end, the first end of each deflectable member extending from the main body at positions about the perimeter of the side opening.

10. The stent of claim 1, wherein the body wall comprises a plurality of circumferential rings, the plurality of rings being longitudinally offset from one another about the main longitudinal axis, and wherein
    at least two adjacent circumferential rings are connected to one another by at least one bioabsorbable stent member, and wherein
    at least one circumferential ring adjacent the perimeter of the side opening is connected to the perimeter by at least one bioabsorbable stent member.

11. The stent of claim 10, further comprising a plurality of deflectable members, each deflectable member having a first end and a second end, the first end of each deflectable member extending from the main body at positions about the perimeter of the side opening, wherein
    at least one circumferential ring is engaged to the perimeter of the side opening, and wherein
    the at least one circumferential ring adjacent the perimeter of the side opening connected to the perimeter by at least one bioabsorbable stent member being also connected by at least one bioabsorbable stent member to the at least one circumferential ring engaged to the perimeter of the side opening.

12. The stent of claim 1, further comprising a plurality of bioabsorbable stent members, the plurality of bioabsorbable stent members substantially covering the side opening.

13. A bifurcated stent, the stent having an unexpanded state and an expanded state, the stent comprising:
    a main body with a body wall, the body wall extending along a main longitudinal axis from a proximal end to a distal end and defining a lumen therethrough, the body wall comprised of interconnected stent members, a plurality of the interconnected stent members defining a plurality of cells, at least one of the plurality of cells being a side opening, the side opening being shaped differently then the other cells of the stent;
    a first branch having a first branch body, the first branch body extending along a first branch longitudinal axis when the stent is in the expanded state, the first branch body extending from the body wall from at least a first region adjacent the side opening and a second region adjacent the side opening, the first branch body comprised of interconnected stent members; and
    a second branch having a second branch body, the second branch body extending along a second branch longitudinal axis when the stent is in the expanded state, the second branch body comprised of interconnected stent members, wherein
    the first branch body and the second branch body extend from the main body at the distal end of the main body, and wherein
    at least one of the stent members of the first branch body and the second branch body being connected to the main body at the distal end by at least one bioabsorbable stent member, and at least one of the stent members of the first branch body comprising a bioabsorbable stent member that substantially covers the side opening.

14. The stent of claim 13, wherein the main body has a main diameter, the first branch body has a first branch diameter, and the second branch body has a second branch diameter, at least one of the first branch diameter and the second branch diameter being substantially equal to or greater than the main diameter.

15. A stent, the stent having an unexpanded state and an expanded state, the stent comprising:
    a main body with a body wall, the body wall extending along a main longitudinal axis from a proximal end to a distal end and defining a lumen therethrough, the body wall comprised of interconnected stent members, a plurality of the interconnected stent members defining a plurality of cells, at least one of the plurality of cells being a side opening, the side opening being shaped differently then the other cells of the stent, the side opening having a perimeter, wherein the perimeter is bioabsorbable and at least one of the interconnected stent members of the side opening is bioabsorbable, the at least one bioabsorbable stent member of the side opening substantially covering the side opening.

* * * * *